United States Patent [19]
Gilby et al.

[11] Patent Number: 5,761,952
[45] Date of Patent: Jun. 9, 1998

[54] ELECTROCHEMICAL GAS SENSOR

[75] Inventors: Jonathan Howard Gilby, West Sussex; John Robert Finbow, Hampshire, both of United Kingdom

[73] Assignee: City Technology Limited, Portsmouth, United Kingdom

[21] Appl. No.: 745,498

[22] Filed: Nov. 12, 1996

[30] Foreign Application Priority Data

Nov. 23, 1995 [GB] United Kingdom ............ 9523963

[51] Int. Cl.$^6$ ............................................. G01N 27/00
[52] U.S. Cl. ................................... 73/1.06; 73/1.07
[58] Field of Search ........................ 73/1.02, 1.03, 73/1.04, 1.05, 1.06, 1.07, 23.21; 324/555, 601, 74

[56] References Cited

U.S. PATENT DOCUMENTS

| | | | |
|---|---|---|---|
| 4,527,583 | 7/1985 | Simpson | 73/754 |
| 4,532,013 | 7/1985 | Dietz et al. | 204/401 |
| 4,557,269 | 12/1985 | Reynolds et al. | 128/675 |
| 4,914,424 | 4/1990 | Hirao | 340/632 |
| 5,135,002 | 8/1992 | Kirchner et al. | 73/766 |
| 5,202,637 | 4/1993 | Jones | 324/425 |
| 5,347,476 | 9/1994 | McBean, Sr. | 73/1.88 |
| 5,421,189 | 6/1995 | Dussault | 73/19.1 |

FOREIGN PATENT DOCUMENTS

| | | |
|---|---|---|
| 0 079 498 | 5/1983 | European Pat. Off. . |
| 35 44 034 | 6/1987 | Germany . |
| 2 284 059 | 5/1995 | United Kingdom . |

*Primary Examiner*—Hezron E. Williams
*Assistant Examiner*—Nashmiya Fayyaz
*Attorney, Agent, or Firm*—Lee, Mann, Smith, McWilliams, Sweeney & Ohlson

[57] ABSTRACT

An electrochemical gas sensor having a housing in which components of the sensor are mounted. A number of electrical connectors are secured to the housing and coupled to respective sensor components enabling the sensor to be connected to a sensor monitoring system for monitoring an electrical output from the sensor and for determining gas concentration. The housing includes one or more indicating formations whose position on the housing causes an appropriate calibration parameter to be selected.

8 Claims, 4 Drawing Sheets

ELECTROCHEMICAL GAS SENSOR

FIELD OF THE INVENTION

The invention relates to an electrochemical gas sensor of the kind comprising a housing in which components of the sensor are mounted; and a number of electrical connectors secured to the housing and coupled to respective sensor components enabling the sensor to be connected to a sensor monitoring system for monitoring an electrical output from the sensor. Such gas sensors are hereinafter referred to as of the kind described.

DESCRIPTION OF THE PRIOR ART

Electrochemical gas sensors of the kind described are used in a wide variety of fields for detecting different gases such as oxygen and toxic gases such as carbon monoxide and hydrogen sulphide. They can be used for detecting gas composition and/or concentration. The sensors may comprise two, three or four electrode sensors depending upon application. In order to determine the gas composition and/or concentration monitored by the sensor, it is necessary to connect the electrodes into an electrical circuit and then to monitor current flowing through the circuit. Gas concentration is typically determined by passing the current through a resistor and monitoring the voltage drop across the resistor. This voltage drop is then converted to a gas concentration value. Although each sensor is constructed in a similar manner, there is inevitably a small variation in the response or sensitivity of different sensors in terms of the variation of current with gas concentration. Since the processing electronics apply a standard conversion algorithm to the monitored voltage drop to obtain a gas concentration value, it is necessary to adjust or calibrate the resistor so that it is suited to the connected sensor and will generate the voltage drop required by the processing electronics corresponding to a predetermined gas concentration.

In the past, this has been achieved by exposing the sensor to a test gas of known concentration and then adjusting the resistor, which could be a potentiometer or resistor bank, while viewing a display of concentration value until the display indicates the correct concentration. The problem with this approach is that it requires the use of test gases and skilled engineers who set the resistor correctly.

One approach for dealing with this problem is for the correct resistor value to be determined during manufacture of the sensor, this value then being supplied to the customer with the sensor so that he can then set the resistor accordingly. This could be achieved by supplying a certificate carrying the resistor information but this still requires that the customer sets the resistor value correctly. Including the information within an on-board memory chip is described in GB-A-2284059 but this involves the added cost and complexity of the chip. There is always a risk that the resistor could be set incorrectly leading to erroneous gas concentration readings.

SUMMARY OF THE INVENTION

In accordance with one aspect of the present invention, in an electrochemical gas sensor of the kind described, the housing includes one or more indicating formations whose position on the housing causes an appropriate calibration parameter to be selected.

The invention avoids the need for the customer or an engineer to make any decision in connection with the selection of an appropriate calibration parameter. This is automatically determined by the one or more indication formations on the housing. These formations can be provided during manufacture of the gas sensor and in accordance with the sensitivity of the gas sensor as determined during the manufacturing process.

The or each indicating formation may be defined by a number (usually one) of the electrical connectors. Thus, during manufacture, one or more of the electrical connectors are positioned on the housing at a location corresponding to the determined sensitivity of the sensor. Typically, where a single indicating formation is utilized, this is defined by the electrical connector connected to the counter electrode of the sensor.

Alternatively, the indicating formation(s) can be provided separate from the electrical connectors.

Conveniently, the or each indicating formation is in the form of a pin but it is possible for other types of indicating formation to be utilized. For example, the indication formation could be determined by the overall shape of the housing.

In a further example, the indicating formation comprises an electrical pad.

A sensor according to the invention can be used in a gas monitoring system which further comprises a sensor monitoring system to which the sensor can be connected, the sensor monitoring system having means for detecting the location of the or each indicating formation on the housing and for causing signals from the sensor to be processed using the indicated calibration parameter.

In the preferred example, the indicating formation is provided by one of the electrical connectors and the sensor monitoring system includes a number of different resistances each connected on one side to a respective coupling location and on the other side to a common signal processing circuit, the location on the sensor of the electrical connector defining the indicating formation being chosen to correspond to the coupling location connected to the resistance required for suitably calibrating the output signal from the sensor. This provides a very simple, mechanical method of selecting the appropriate resistance.

In other examples, the sensor monitoring system further includes processing means for determining gas composition and/or concentration in response to electrical signals supplied from the sensor, the processing means being adapted to select a previously stored calibration parameter in accordance with the determined position of the or each indicating formation.

In this case, the or each indicating formation is used to control operation of the processing means. The processing means could select a suitable gain value as a calibration parameter or cause an appropriate resistance to be inserted into the electrical circuit to which electrical signals to the sensor are applied.

Although, in general, a single indicating formation will be used, it is possible to use more than one. For example, two or more could be used selectively to define a digital code or binary value.

In accordance with a second aspect of the invention, a method of manufacturing an electrochemical gas sensor comprises:

a) providing a housing in which are mounted components of the sensor, the housing having a number of electrical connectors secured to it and coupled to respective sensor components enabling the sensor to be connected to a sensor monitoring system for monitoring an electrical output from the sensor;

b) performing a calibration test on the gas sensor; and, c) providing one or more indicating formations on the housing whose position causes an appropriate calibration parameter to be selected by the sensor monitoring system.

As with the first aspect of the invention, the advantage of this approach lies in carrying out the calibration test at the manufacturing stage and providing one or more indicating formations in accordance with the calibration test so that the user can easily operate the sensor with the correct calibration parameter.

The indicating formation(s) can be provided in any of the ways described above but in the preferred arrangement, step (c) comprises mounting a calibration member on the housing, the calibration member carrying an electrical pad which is positioned at a location corresponding to the result of the calibration test in step (b).

This leads to a particularly convenient manufacturing method where the manufacturer simply has to mount a calibration member on the housing in the correct orientation.

In some cases, a single calibration member could be provided whose orientation on the housing is determined by the manufacturer in accordance with the calibration test. Conveniently, however, the method further comprises selecting the calibration member from a set of calibration members, each calibration member in the set being connectable to the housing in only one orientation and carrying an electrical pad which, when the calibration member is mounted on the housing, is at a unique location relative to the location of the electrical pad of other members of the set when mounted on the housing. With this approach, the manufacture is provided with a set of calibration members and he simply has to choose the calibration member corresponding to the desired calibration parameter which can then only be fitted to the housing in one orientation thus automatically locating the electrical pad in the correct position.

The calibration member can be located on the housing by aligning appropriate markings or the like but preferably the calibration member and the housing have complementary formations to determine the manner in which the calibration member is located on the housing. This reduces the risk of misalignment.

In some cases, special complementary formations could be provided on both the calibration member and the housing but conveniently the complementary formations are defined by the electrical connectors on the housing and one or more recesses formed in the calibration member through which the electrical connectors extend.

BRIEF DESCRIPTION OF THE DRAWINGS

Some examples of gas monitoring systems incorporating electrochemical gas sensors according to the invention will now be described with reference to the accompanying drawings, in which.

DETAILED DESCRIPTION OF THE EMBODIMENTS

Figure 1:
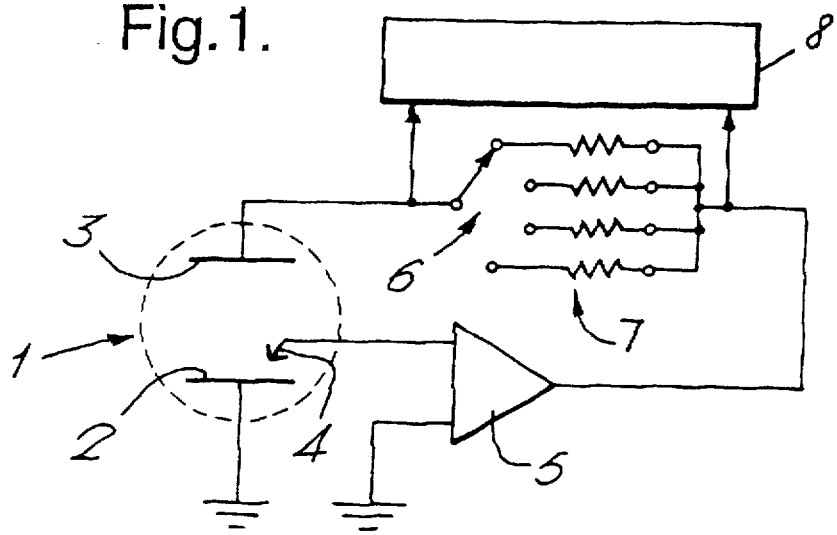
FIG. 1 is a block circuit diagram of a first example.
Figure 2:
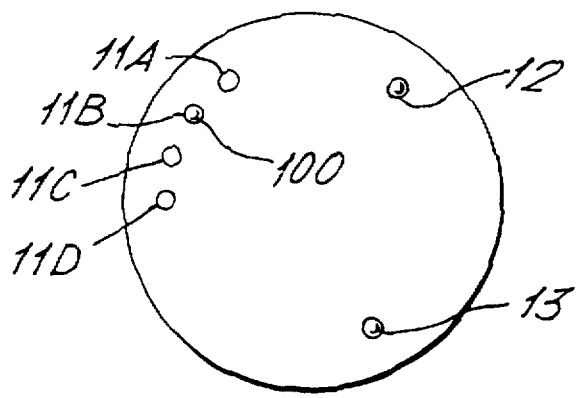
FIG. 2 is an underneath plan of a sensor for use in the first example.
Figure 3:
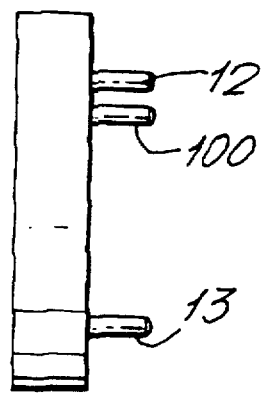
FIG. 3 is a side view of the sensor shown in FIG. 2.

FIG. 1 illustrates in block circuit diagram form a gas monitoring system which includes an electrochemical gas sensor 1 of conventional form and including a sensing electrode 2, a counter electrode 3, and a reference electrode 4. Such electrochemical gas sensors are very well known and are marketed by the applicants, City Technology Limited, for detecting gases such as oxygen and toxic gases. The sensor 1 is connected into an electrical circuit such that the reference electrode is connected to one input of an operational amplifier 5 while the other input of the operational amplifier 5 is connected to ground. The sensing electrode 2 is connected to ground while the counter electrode 3 is connected to a switch 6. The switch 6 can connect the counter electrode 3 to one of a number of resistances 7 in a bank of resistances, each of the resistances being connected to the output of the operational amplifier 5. The voltage drop across the resistances 7 is monitored by a voltmeter 8 which provides a gas concentration value display directly in ppm.

Typically, a toxic gas sensor, for example for monitoring the concentration of carbon monoxide, will generate an output current in the range 1.5 to 4.5 microamps in response to a gas concentration of 100 ppm. However, the actual output current for a given gas sensor will vary within this range and conventionally, as described above, this would normally have been determined at a customer site by exposing the gas sensor to a known concentration of gas and monitoring the output current. An appropriate one of the resistances 7 is then selected using the switch 6 so that the voltage drop across the resistances 7 will correspond to a calibration value which enables the voltmeter 8 to display a gas concentration value.

Figure 4:
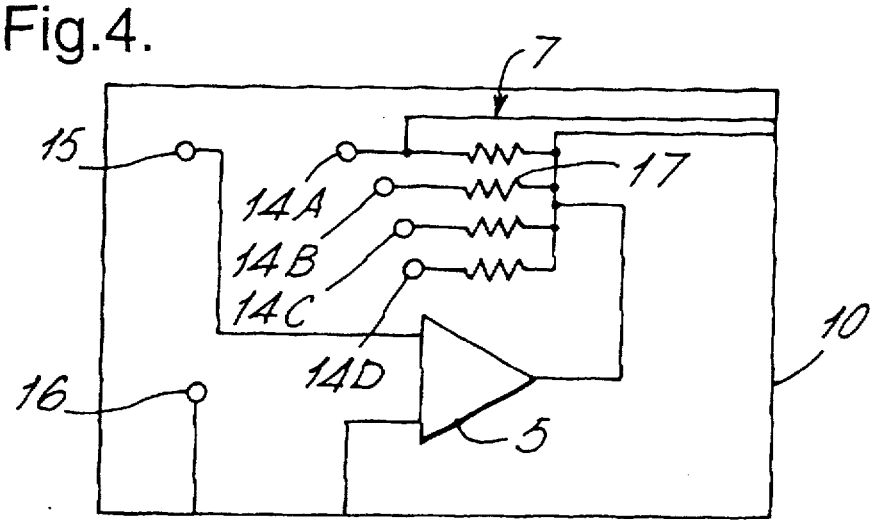
FIG. 4 is a schematic view of a printed circuit board for use with the sensor shown in FIGS. 2 and 3.

In the example of the invention to be described, the setting of the switch 6 is achieved automatically upon inserting the sensor 1 into a printed circuit board 10 (FIG. 4) carrying the electrical circuit of FIG. 1. During manufacture, the sensitivity of the sensor 1 is determined and in accordance with that determined sensitivity, an electrical connecting pin 100 is located in a respective one of a number of location apertures 11A–11D each of which is connected to the counter electrode 3. In the example shown, the pin 10 is located in the aperture 11B. In addition, pins 12,13 are provided connected to the counter and sensing electrodes 3,2 respectively.

The sensor 1 is located in use on a printed circuit board 10 which includes the amplifier 5 and resistances 7. Each of the resistances 7 is coupled to a respective socket 14A–14D. A further pair of sockets 15,16 are provided connected to the operational amplifier 5 and ground respectively. When the sensor 1 is mounted on the printed circuit board 10, the pins 12,13 locate into the sockets 15,16 respectively while the pin 100 locates in the socket 14B. This connects the counter electrode 3 with the resistance 17 which was chosen such that the voltage drop monitored by the voltmeter 8 (connected to the resistances 7) is calibrated automatically.

Figure 5:
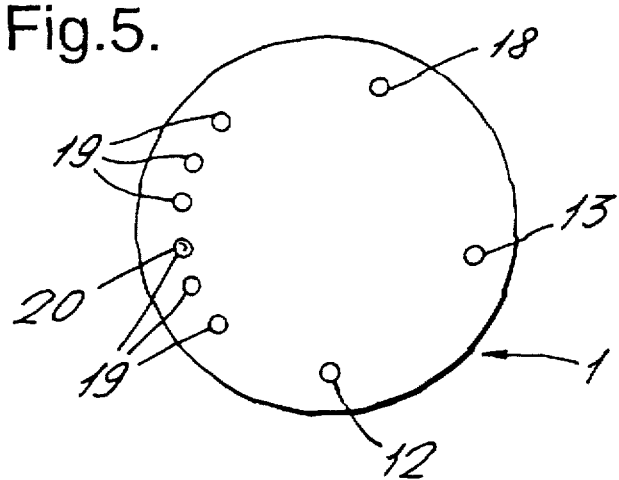
FIG. 5 is a view similar to FIG. 2 but of a second example.
Figure 6:
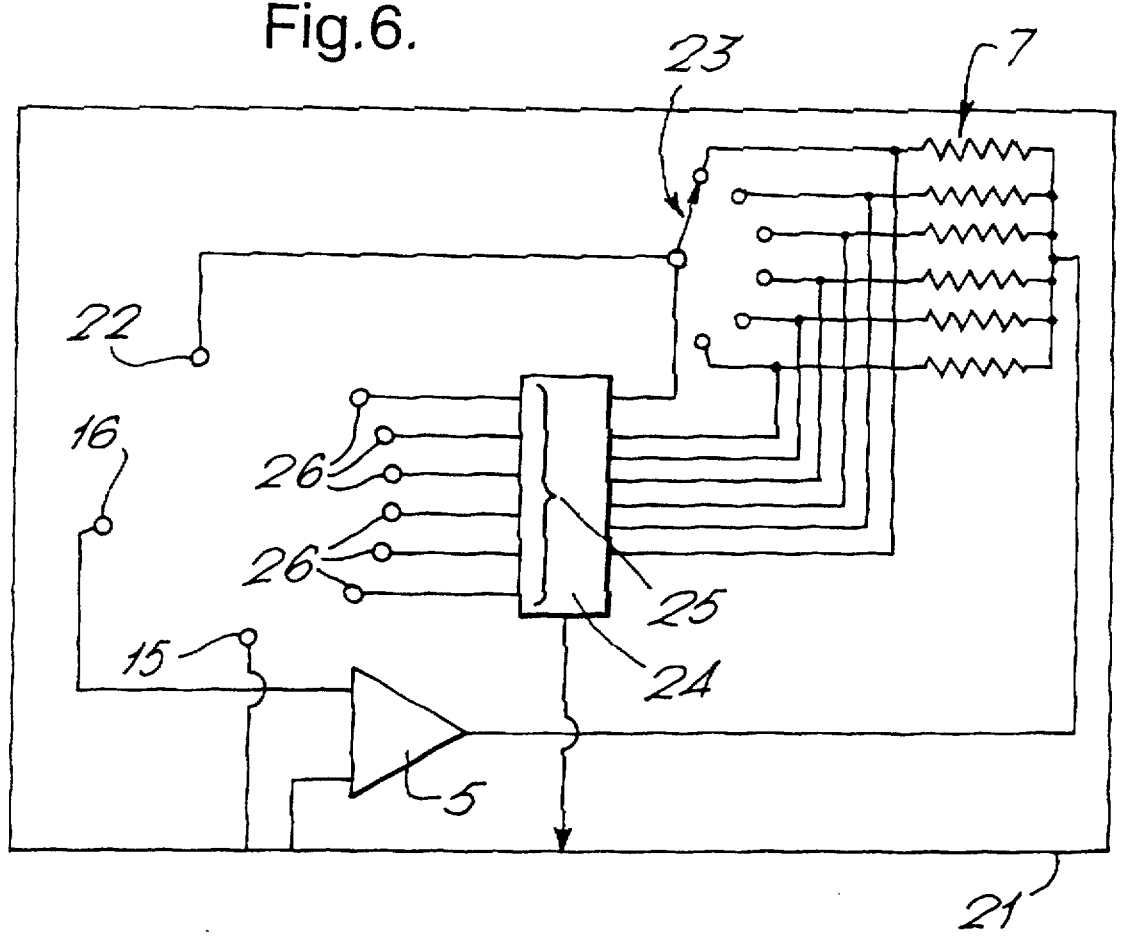
FIG. 6 is a schematic view of a printed circuit board for use with the sensor shown in FIG. 5.

The example described is particularly advantageous since it utilizes the connection pin 100 connected to the counter electrode 3 to select the appropriate resistance 7. The example shown in FIGS. 5 and 6 illustrates an arrangement in which an additional pin, which may be a non-conducting plastics pin or the like, is formed on the underside of the sensor at a location corresponding to the sensitivity of the sensor. Thus, as shown in FIG. 5, the underside of the sensor is provided with pins 12,13 as before and a pin 18 connected to the counter electrode. In addition, there are a number of pin location positions 19 provided. During manufacture, the sensitivity of the cell is determined as before and a plastics pin is positioned at an appropriate location 19 corresponding to the sensitivity of the cell. In this example, a pin 20 is shown at one of the locations 19. A printed circuit board 21 is shown in FIG. 6 to which the sensor 1 of FIG. 5 is mounted in use. This includes apertures 15,16 into which the pins 12,13 respectively locate and an aperture 22 in which the pin 18 locates. The aperture 22 is connected to a switch 23. In this case, a microprocessor 24 is provided having a set of inputs 25 connected to respective apertures 26 corresponding to the pin locations 19. When the sensor 1 is mounted on the printed circuit board 21, the pin 20 will locate in an appropriate one of the apertures 26. The microprocessor 24 is continually polling its inputs and will detect in a conventional manner which of the apertures 26 has received the pin 20 (for example the pin 20 could mechanically close a switch associated with the aperture). In accordance with that information, the microprocessor 24 will then actuate the switch 23 to cause it to connect the counter electrode 3 with the appropriate one of the resistances 7. The microprocessor 24 will then monitor the voltage drop across the resistances 7 in a conventional manner and cause the display 9 to be actuated, as before.

In another example (not shown), a single resistance could be provided in the electrical circuit connected with the counter electrode 3. Otherwise, this example will be similar to that shown in FIGS. 5 and 6 and the microprocessor 24 will respond to the aperture 26 which receives the pin 20 to select an appropriate calibration factor which is used during the conversion of the voltage drop value to a gas concentration value.

Figure 7:
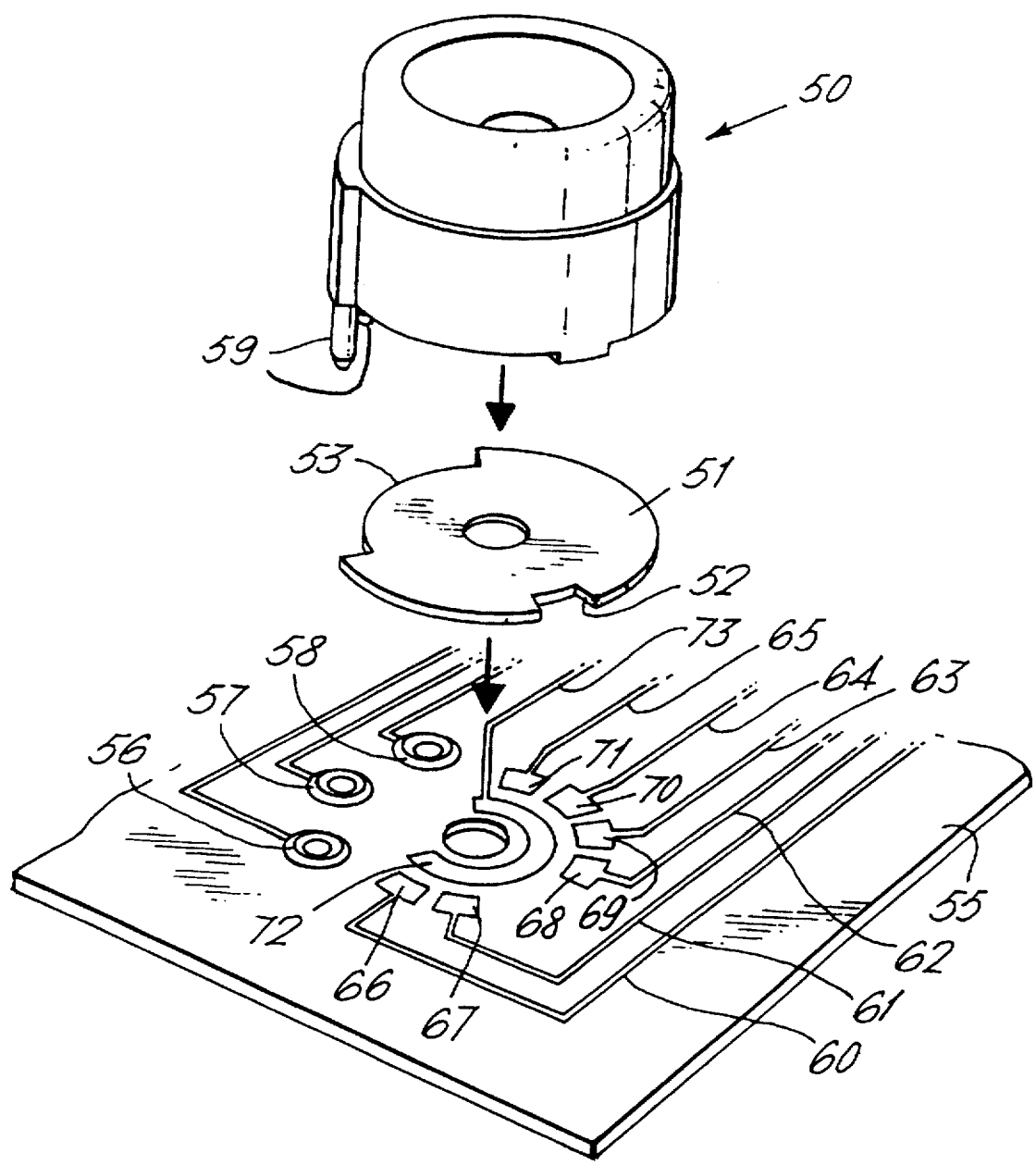
FIG. 7 is an exploded, schematic view of a third example of a gas monitoring system; and, FIG. 8 illustrates six different sensor plates for use with the sensor shown in FIG. 7.
Figure 8:
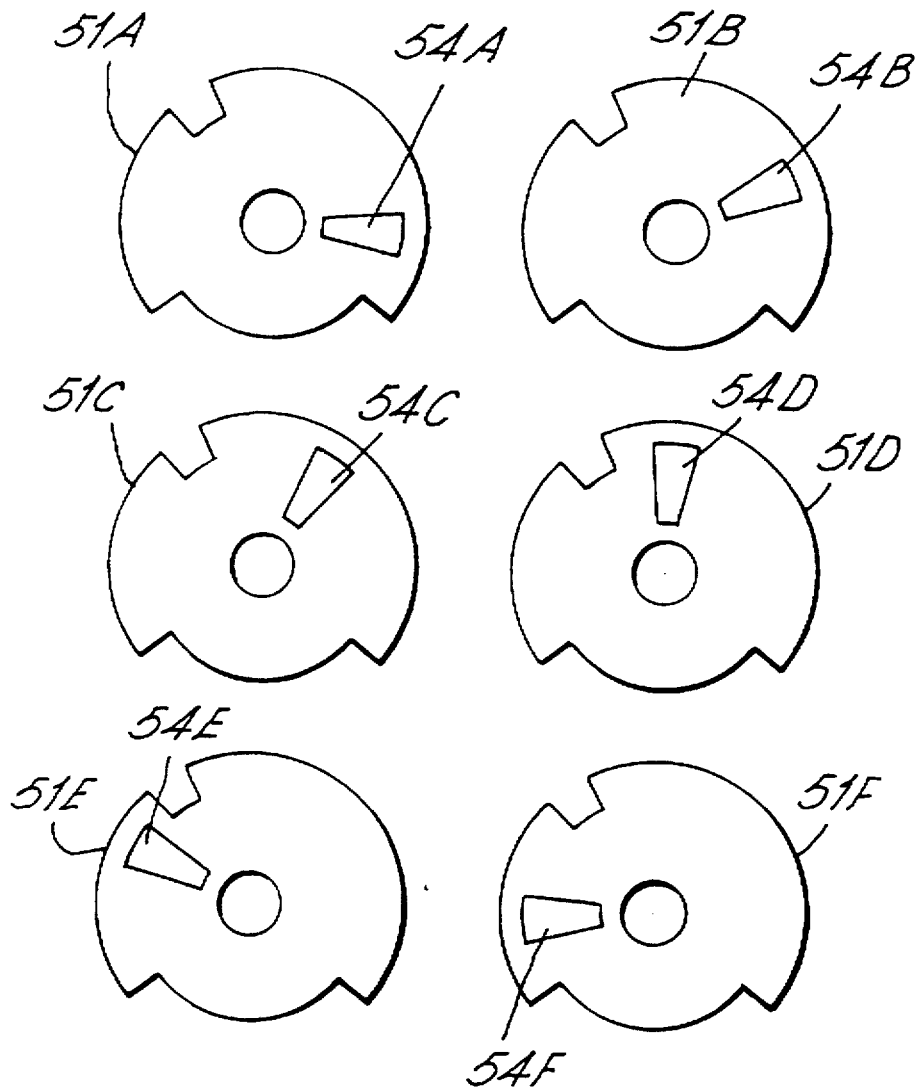

A further example of a gas monitoring system is shown in FIGS. 7 and 8. In this example, a gas sensor similar to the sensor 1 of the earlier examples is illustrated at 50. A 0.5 mm thick acetate plate 51 is bonded via adhesive to the underside of the sensor 50 (although shown exploded in FIG. 7). The plate 51 has a notch 52 and a recess 53 in its outer periphery. The notch 52 locates the plate in the correct position on the underside of the sensor 50 while the recess 53 permits the three pins 59 connected to the electrodes of the sensor 50 to protrude below the plate 51. The underside of the plate 51 is provided with an electrical pad printed using conductive ink and located at a circumferential position dependent upon the appropriate calibration of the sensor 50. When the sensor 50 is manufactured, an appropriate plate 51 is selected in accordance with the calibration process. FIG. 8 illustrates six alternative plates 51A–51F each carrying an electrical pad 54A–54F at a different location relative to the notch 52 and recess 53.

In use, the sensor 50 with adhered plate 51 is located into a printed circuit board 55 having three pin sockets 56–58 for receiving the respective pins 59 (only two shown) of the sensor 50. In addition, the board 55 carries six conductive tracks 60–65 terminating in respective contact pads 66–71. The board 55 also carries a U-shaped contact 72 insulated from the contacts 66–71 and connected to a track 73.

When the sensor 50 and plate 51 are located onto the board 55, the pins 59 are received in the sockets 56–58 and the conductive pad 54A–54F will extend between the contact 72 and a respective one of the contacts 66–71 depending upon the position of the pad. This connection is then detected by a processor (not shown) which monitors the tracks 60–65 and 73 and the processor then chooses an appropriate calibration in a similar manner to the system described in FIGS. 5 and 6.

We claim:

1. A gas monitoring system including an electrochemical gas sensor comprising a housing in which components of the sensor are mounted; a number of electrical connectors secured to said housing and coupled to respective sensor components enabling the sensor to be connected to a sensor monitoring system for monitoring an electrical output from the sensor, said housing including at least one indicating formation whose position on the housing is indicative of an appropriate calibration parameter; and a sensor monitoring system separate from but connectable to said sensor, said sensor monitoring system having means for detecting the position of said at least one indicating formation on said housing and for causing signals from said sensor to be processed using the calibration parameter indicated by said detected position of said at least one indicating formation.

2. A gas monitoring system according to claim 1, wherein said sensor monitoring system further includes processing means for determining gas composition and/or concentration in response to electrical signals supplied from said sensor, said processing means being adapted to select a previously stored calibration parameter in accordance with said detected position of said at least one indicating formation.

3. A gas monitoring system according to claim 2, wherein said previously stored calibration parameter is an amplifier gain value to be applied to signals received from said gas sensor.

4. A gas monitoring system according to claim 2, wherein said processing means includes an electrical circuit, and wherein said previously stored calibration parameter is a resistance which said processing means causes to be inserted into said electrical circuit to which electrical signals from the sensor are supplied.

5. A gas monitoring system according to claim 2, wherein said at least one indicating formation defines a binary value which is used by the processing means to determine the calibration parameter.

6. A gas monitoring system according to claim 1, wherein said at least one indicating formation is provided by one of said electrical connectors, and wherein said sensor monitoring system includes a number of coupling locations to which said electrical connectors can be coupled, and a number of different resistances each connected on one side to a respective one of said coupling locations and on the other side to a common signal processing circuit, the location on the sensor of the one electrical connector defining the indicating formation being chosen to correspond to the one coupling location connected to the resistance required for suitably calibrating an output signal from the sensor.

7. A gas monitoring system according to claim 1, wherein said sensor monitoring system includes a printed circuit board to which said sensor is mounted.

8. A gas monitoring system according to claim 7, wherein said indicating formation comprises an electrical pad, wherein said printed circuit board carries a set of contacts individually connected to said detecting means, said electrical pad on said sensor housing electrically connecting a pair of the contacts determined in accordance with the position of the electrical pad.

* * * * *